United States Patent
Hu (10) Patent No.: US 8,849,000 B2
(45) Date of Patent: Sep. 30, 2014

(54) METHOD AND DEVICE FOR DETECTING BRIGHT BRAIN REGIONS FROM COMPUTED TOMOGRAPHY IMAGES

(75) Inventor: Qingmao Hu, Guangdong (CN)

(73) Assignee: Shenzhen Institute of Advanced Technology, Chinese Academy of Sciences, Guangdong (CN)

( * ) Notice: Subject to any disclaimer, the term of this patent is extended or adjusted under 35 U.S.C. 154(b) by 207 days.

(21) Appl. No.: 13/513,453

(22) PCT Filed: Dec. 4, 2009

(86) PCT No.: PCT/CN2009/075320
§ 371 (c)(1),
(2), (4) Date: Jun. 1, 2012

(87) PCT Pub. No.: WO2011/066689
PCT Pub. Date: Jun. 9, 2011

(65) Prior Publication Data
US 2012/0237103 A1     Sep. 20, 2012

(51) Int. Cl.
*G06K 9/00* (2006.01)
*G06T 7/00* (2006.01)
*G06T 7/60* (2006.01)
*A61B 6/00* (2006.01)
*A61B 6/03* (2006.01)

(52) U.S. Cl.
CPC ............. *G06T 7/0012* (2013.01); *G06T 7/608* (2013.01); *G06T 7/0091* (2013.01); *A61B 6/03* (2013.01); *A61B 6/501* (2013.01); *G06T 2207/30016* (2013.01); *G06T 7/0081* (2013.01); *G06T 2207/20148* (2013.01); *G06T 2207/10081* (2013.01); *G06T 7/602* (2013.01)
USPC ....................................... 382/131

(58) Field of Classification Search
None
See application file for complete search history.

(56) References Cited

U.S. PATENT DOCUMENTS

| 6,819,735 B2 | 11/2004 | Bruder et al. |
| 2007/0031020 A1 | 2/2007 | Li |
| 2008/0021502 A1 * | 1/2008 | Imielinska et al. ............... 607/1 |

FOREIGN PATENT DOCUMENTS

| CN | 1907225 A | 2/2007 | |
| CN | 101238987 A | 8/2008 | |
| WO | WO/2009/110850 | * 9/2009 | ............ 382/131 |
| WO | WO 2009/110850 A1 | 9/2009 | |

* cited by examiner

*Primary Examiner* — Bhavesh Mehta
*Assistant Examiner* — Siamak Harandi
(74) *Attorney, Agent, or Firm* — Birch, Stewart, Kolasch & Birch, LLP (57) ABSTRACT

A method and devices are disclosed to detect bright brain regions (BBRs) from clinical non-enhanced computed tomography images through large grayscale, large grayscale asymmetry with respect to the midsagittal plane (MSP), and large grayscale local contrast. An adaptive approach is disclosed to determine thresholds of the 3 features and adjust the window width for data conversion. The substantial grayscale variability of BBRs for a subject is addressed by finding the bright portion followed by recovering. Those BBR voxels symmetrical to the MSP are recovered, partial volume effects are compensated and the high grayscale regions which may not correspond to intracerebral hemorrhage are excluded. The disclosed method and system could be a useful tool to aid classifying stroke types, quantifying intracerebral hemorrhage and enhancing stroke therapy.

17 Claims, 3 Drawing Sheets

METHOD AND DEVICE FOR DETECTING BRIGHT BRAIN REGIONS FROM COMPUTED TOMOGRAPHY IMAGES

FIELD OF THE INVENTION

The present invention relates to a medical image processing technology, in particular, relates to a method and a device for detecting the bright brain regions of a patient utilizing computed tomography (CT) images.

BACKGROUND OF THE INVENTION

Strokes are either ischemic or hemorrhagic. Because the management of these subtypes is so different, the clinical distinction among the subtypes is one of the most important and urgentest steps in stroke management.

Intracerebral hemorrhage (ICH) is an acute and spontaneous extravasation of blood into the brain parenchyma. It accounts for 10-30% of all stroke admissions to hospital, and leads to catastrophic disability, morbidity, and a 6 month mortality of 30-50%.

The presentation of ICH is very variable and is indistinguishable from ischemic stroke on clinical grounds alone, making neuro-imaging absolutely necessary. CT has become part of the standard evaluation of ICH because of its wide availability, short scan time, and easy interpretation. Thus the first step for patients with stroke-like symptoms is to determine if there is hemorrhage from non-enhanced CT images.

Non-enhanced CT or simply CT is the recommended modality for the diagnosis of ICH. ICH exhibits hyperdensity, which can generally be recognized by experienced radiologists. Diagnosis of ICH from CT can be difficult when the lesion is small or is masked by normal structures or when the reader is inexperienced which is the case in emergency setting. An estimation of hematoma volume is extremely useful in predicting the patient's clinical course and directing management. The technical challenges for automatic delineation of ICH include 1) existence of non-ICH voxels with similar intensity to ICH, such as skull, calcification and streaks; 2) ICH itself exhibits large variation in grayscales, i.e., voxels around the boundary of an ICH region are darker and the grayscale is smaller when ICH enters ventricles; 3) models such as brain atlas are difficult to be directly incorporated due to the large voxel size and pathological nature of the clinical CT data; 4) the mass effect, deformation of brain tissues and spontaneous movement during scanning making the segmentation and anatomical localization of ICH hard.

Currently, CT has been widely adopted for differentiating ischemic or hemorrhagic stroke. However, report on quantifying hemorrhage from CT is scarce. Loncaric et al (Loncaric S, Dhawan A P, Broderick J, Brott T. 3-D image analysis of intra-cerebral brain hemorrhage from digitized CT films. Computer Methods and Programs in Biomedicine 1995; 46: 207-216) employed a semi-automatic method to determine ICH through 3 steps: determining the gray level ranges of background, brain tissues and skull by k-means method; choosing two fixed intensity thresholds (50 and 130) to remove skull through mathematical morphological operations; and selecting a seed point of ICH manually, together with the user-specified intensity threshold, to grow the ICH region. This method has several limitations including 1) user intervention is needed for setting key parameters (seed point and intensity thresholds), which may yield different ICH for different users; 2) mathematical morphological operations with fixed structuring element may not be able to remove the skull due to the ICH; and 3) fixed thresholds to grow ICH may under-segment or over-segment. Chan (Chan T, Huang H K. Effect of a computer-aided diagnosis system on clinicians' performance in detection of small acute intracranial hemorrhage on computed tomography. Academic Radiology 2008; 15 (3): 290-299) developed an image analysis system to delineate small acute intracranial hemorrhage, which cannot be extended for non-small ICH due to possible deformation and mass effect. However, it is shown by Chan and Huang (Chan T, Huang H K. Effect of a computer-aided diagnosis system on clinicians' performance in detection of small acute intracranial hemorrhage on computed tomography. Academic Radiology 2008; 15 (3): 290-299) that the system can improve the clinicians' performance in detecting acute ICH on CT. At present, the volume and anatomical localization of ICH are approximated manually from CT slices. This suffers from being tedious and laborious, requiring readers of CT to be an expert in neuron-radiology, and inability to control accuracy and to provide accurate 3D shape information of the ICH.

SUMMARY OF THE INVENTION

The objective of this intervention is to localize and quantify the bright brain regions which are likely ICH voxels from CT images to aid differentiation between ischemic and hemorrhagic strokes and assist the decision in making regarding the treatment of hemorrhagic stroke patients.

A method for detecting the bright brain regions from computed tomography images comprises: loading computed tomography images data; deriving the skull images; deriving the brain images; converting said brain images to the lower bit images data; calculating the generalized asymmetry map with respect to the midsagittal plane; calculating grayscale threshold, threshold of local contrast, threshold of asymmetry, and threshold of partial volume voxels for bright brain regions; deriving initial bright brain regions; recovering bright brain voxels symmetrical to the midsagittal plane; refining the initial bright brain regions; checking if the detected BBRs is low or high in average grayscale and the window width being increased or decreased when the detected BBRs is low or high in average grayscale and going back to the converting step; and outputting the bright brain regions.

A device for detecting the bright brain regions from computed tomography images comprises: an input unit loading computed tomography images data; a first deriving unit deriving the skull images; a second deriving unit deriving the brain images; a convertor converting said brain images to the lower bit images data; a first calculator calculating the generalized asymmetry map with respect to the midsagittal plane; a second calculator calculating grayscale threshold, threshold of local contrast, threshold of asymmetry, and threshold of partial volume voxels for bright brain regions; a third deriving unit derive initial bright brain regions; a recovering unit recovering bright brain voxels symmetrical to the midsagittal plane; a refining unit refining the initial bright brain regions; a judging unit checking if the detected BBRs is low or high in average grayscale and the window width being increased or decreased when the detected BBRs is low or high in average grayscale and going back to the converting step; and an output unit outputting the bright brain regions.

An algorithm is proposed which consists of the following steps: skull peeling through intensity thresholding and mathematical morphology; adaptive selection of the original image, brain structures or head structures for calculating the midsagittal plane (MSP) according to the number of detected inlier symmetrical points on axial slices; determination of AIH candidate regions based on AIH's high intensities, high intensity asymmetry with respect to the MSP, and being brighter than their surrounding brain tissues; removal of calcification and linear streaks, and compensation of partial volume effects.

Conclusion of the proposed algorithm is fast (less than 20 seconds on a PC with 2.21 GHz CPU) automatic and accurate, and could be employed for the diagnosis and curing of AIH patients.

Skull can be used as an intermediate result for medical experts to diagnose skull fracture as well as traumatic brain fracture.

In the 16-bit data, skull can be differentiated from other bright brain regions (BBRs) such as hemorrhage as the former is much larger in grayscales. To differentiate other bright brain regions such as hemorrhage and normal brain tissues (gray mater and white mater), a small window width should be used. This small window width makes it impossible to differentiate skull and other bright brain regions. To be able to differentiate the bright brain regions close to the skull and the skull, the conversion from 16-bit to 8-bit should be done after the skull is extracted.

Bright brain regions (BBRs) vary in grayscales due to pathology or external imaging conditions. For example, hemorrhage in its acute stage will be brighter than the hemorrhage in non-acute stage, a CT scanner with bad calibration may have higher CT values than normal CT scanners. Judging the normal range of BBRs will be able to compensate these changes: for example, if the detected BBRs have a small average grayscale, it may correspond to hemorrhage in the non-acute stage, and thus needs a smaller window width to increase the contrast between the BBRs and its neighboring normal brain tissues; if the CT value is higher than normal, the detected BBRs may have a higher average, and thus it is desirable to increase the window width to decrease the contrast between the BBRs and its neighboring normal brain tissues.

BRIEF DESCRIPTION OF THE DRAWINGS

FIG. 3 shows the brain image of the axial slice of FIG. 2a.

FIG. 5b shows the detected BBR of FIG. 5a.

FIG. 6b shows the existing BBRs of FIG. 6a.

FIG. 7b shows the asymmetrical bright brain region delineated of FIG. 7a.

DESCRIPTION OF THE PREFERRED EMBODIMENT

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Figure 1:
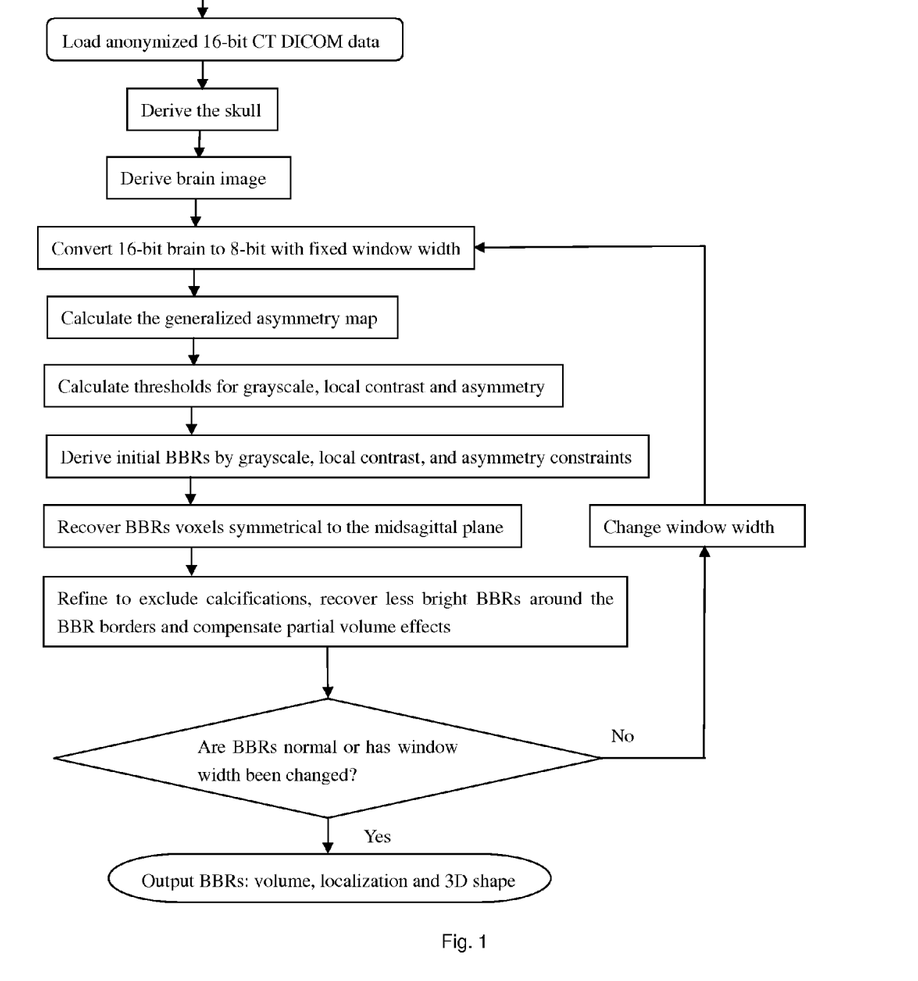
FIG. 1 shows a flowchart of the disclosed method, where BBR stands for bright brain region.

The method or device of the present invention takes anonymized DICOM (Digital Imaging and Communication in Medicine, 16-bits) CT images as input, removes the skull from the original 16-bit data, then converts the remaining images into 8-bit with default window width and window center. Subsequently, the average grayscale of the detected bright brain regions (BBRs) is checked to see if it falls within a reasonable range. If no, another round is iterated by changing the window width of the data conversion. The algorithm consists of: derivation of the skull; derivation of the brain to confine the locations of BBRs; description of the BBRs in terms of high grayscale, large grayscale asymmetry with respect to the midsagittal plane (MSP), and large local grayscale contrast; recovering BBRs which are symmetrical to the MSP; excluding those high grayscale voxels which may not correspond to ICH such as calcifications; recovering less bright BBR voxels around the border of the BBR region and compensating partial volume effects. FIG. 1 is the flow chart of the method of the present invention.

The coordinate system (XYZ) corresponds to the following convention: X runs from patient's right to left, Y runs from anterior to posterior, and Z runs from superior to inferior directions.

Step #1: Loading Anonymized 16-bit CT DICOM Data

It comprises loading the head CT images data of a subject/patient suspected to have hemorrhagic stroke from any commercialized CT scanner in the conventional DICOM format. The numbers of voxels in the x, y, and z directions are derived from the DICOM header and are, respectively denoted as xSize, ySize, and zSize. The voxel sizes in x, y, and z directions are also derived and denoted as voxX, voxY, and voxZ, respectively, with a unite of mm/voxel. The 16-bit CT image data is derived and denoted as orgDV(x, y, z), with x, y, z all being integers satisfying $0 \leq x \leq (xSize-1)$, $0 \leq y \leq (ySize-1)$, and $0 \leq z \leq (zSize-1)$.

Step #2: Derivation of the Skull Image

Skull has CT values much higher than that of the hemorrhage. Usually it can be assumed that the CT value of hemorrhage is around 80 Hounsfield Unit (HU) and less than 100 HU. Thus hemorrhage has CT value lower than a constant $T_{skull}$ (say 105 HU). So here any voxel with a CT value greater than $T_{skull}$ is extracted as a voxel of the skull. The skull can be derived from thresholding orgDV(x, y, z) to contain all those voxels with a CT value greater than $T_{skull}=105$ HU.

Figure 2A:
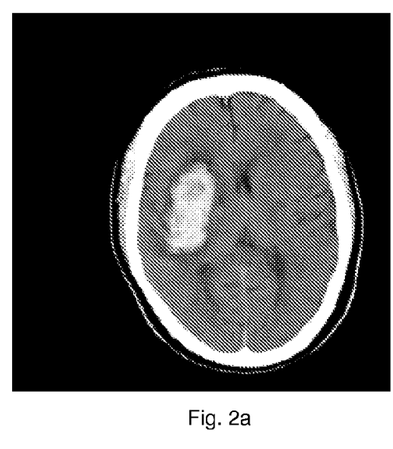
FIG. 2a shows an axial slice with hemorrhage.
Figure 2B:
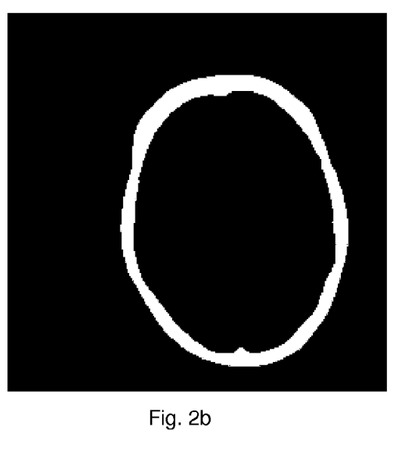
FIG. 2b shows the skull corresponding to FIG. 2a after thresholding.

FIGS. 2a and 2b show an axial slice of a patient with hemorrhage and the corresponding skull after thresholding.

Skull will be employed for analyzing skull fracture and other traumatic brain injury on the one hand; on the other hand, it helps to detect those bright brain regions close to the skull.

Step #3: Derivation of the Brain Images

Fuzzy c-means (FCM) clustering is applied to orgDV(x,y, z) to classify the volumetric data into clusters 1, 2, 3, and 4 with ascending grayscales to get the low and high thresholds to remove non-brain tissues ($T_{low}$, and $T_{high}$, respectively). There are many ways to determine the 2 parameters. One way is to set $T_{low}$ as the maximum intensity of the first cluster, and $T_{high}$ as $T_{skull}$.

The brain is the sum of gray matter (GM), white matter (WM) and cerebrospinal fluid (CSF). It is from where the bright brain regions (BBRs) are to be detected. The brain mask Brain(x, y, z) is calculated in the following way:

Firstly, binarization is achieved through removing both low and high non-brain voxels to derive $B_1(x, y, z)$, i.e., $$B_1(x, y, z) = \begin{cases} 1, & T_{low} < orgDV(x, y, z) < T_{high} \\ 0, & \text{otherwise} \end{cases} \quad (1)$$

Then morphological opening with rectangular structuring element of side 4 mm is applied to $B_1(x, y, z)$ to break the connection between the brain and non-brain tissues to get $B_2(x, y, z)$. The maximum foreground connected component of $B_2(x, y, z)$ is found, whose holes are then filled to get $B_3(x, y, z)$ (a hole is a background region enclosed by foreground regions; filling holes means to change the hole into a foreground region). The neighboring axial slices of $B_3(x, y, z)$ are then automatically checked to exclude isolated foreground regions of $B_3(x, y, z)$ to get the eventual brain mask Brain(x, y, z). An isolated foreground region at axial slice z is a foreground region with less than half of the foreground voxels (x, y, z) having corresponding foreground voxels at its lower and upper axial slices. For the ease of notation, the brain image is also denoted as Brain(x, y, z), which takes the grayscale of orgDV(x, y, z) when (x, y, z) is a brain voxel, or 0 otherwise.

Figure 3:
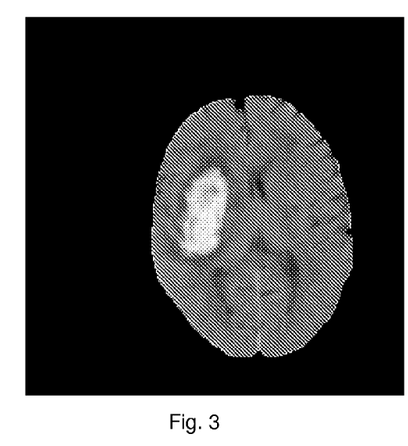

FIG. 3 shows the brain image of the axial slice.

Step #4: Convert the 16-bit Brain Images into 8-bit with Fixed Window Width

Formulate the 8-bit brain data (in orgVolRaw(x, y, z)) for both processing and monitoring with fixed window width (ww) through the following formula $$orgVolRaw(x, y, z) = \begin{cases} 0, & orgDV(x, y, z) < 0 \\ 255 \times \frac{Brain(x, y, z)}{ww} \times orgDV(x, y, z), & 0 \leq orgDV(x, y, z) \leq ww \\ 255, & orgDV(x, y, z) > ww \end{cases} \quad (2)$$

where ww is a constant and is default to 80.

After the data conversion, the 8-bit brain volume orgVolRaw(x, y, z) is classified into clusters 1, 2, 3, and 4 with ascending grayscales by FCM. Subsequently, the following parameters of the four clusters will be used, i.e., the grayscale mean and standard deviation of the third cluster (fcmMean and fcmSd).

Step #5: Calculate the Generalized Asymmetry Map with Respect to the Midsagittal Plane (MSP)

The MSP is a plane to calculate the asymmetry map. Although there are several good algorithms, an algorithm which can handle the possible mass effect, large deformation in grayscale, large midline distortion, and spontaneous movements of hemorrhagic stroke patients from CT hemorrhage images is yet to be explored.

The head mask of the original CT images can be used in case of large distortion of grayscales or spontaneous movements of patients. The head mask can be derived like this: binarization of the volume (a three-dimensional data set) orgDV (x, y, z) (any voxel with a grayscale not less than $T_{low}$ is set to 1 and 0 otherwise; the maximum connected component of the binary image is found and holes within the maximum foreground component are filled to form the head mask). Firstly, the 8-bit volume derived from orgDV(x, y, z) by formula (2) with ww being $T_{skull}$ is explored to extract the MSP, with the local symmetry being defined as the sum of grayscale difference of 10 pairs of searching line segments and outlier removal to handle abnormal grayscale distribution in axial slices; if the number of inliers is less than 6 (which means that image may have serious mass effect or the brain has moved during the scan), each of the head mask is approximated as an ellipse with the long axis being taken as the approximated symmetry line segment to be used for approximating the MSP through outlier removal. The equation of the MSP is denoted as $$ax+by+cz+d=0 \quad (3)$$

where a, b, c, d are calculated parameters with $a > 0$, $a^2+b^2+c^2=1$, and x, y, z, and d all in mm.

The brain exhibits rough symmetry, which is distorted by abnormal grayscale distribution within the brain. The asymmetry may also be due to the extraction error of the MSP. To account for extraction error of the MSP and the possible tilt (which makes the mirrored pair will not be on the same axial slice) during the scan, the generalized asymmetry map is proposed and is defined as the grayscale difference between a voxel and the corresponding mirrored region. In particular, the generalized asymmetry map at (x, y, z) is denoted as asym(x, y, z) and is calculated as $$asym(x, y, z) = \begin{cases} orgVolRaw(x, y, z) - \max(reg(x', y', z)), & orgVolRaw(x, y, z) > \max(reg(x', y', z)) \\ 0, & \text{otherwise} \end{cases} \quad (4)$$

where (x', y', z) is the mirrored point of (x, y, z) with respect to the intersection line (between the MSP and the axial slice z) at axial slice z, max (reg (x', y', z)) is the maximum grayscale of orgVolRaw(x,y,z) within a neighborhood centered at (x', y',z) (7×7 within axial slice z, for instance). When reg(x', y', z) contains no brain voxles, max(reg(x', y', z)) can be taken in several ways. One simple way is to calculate the grayscale average and standard deviation of this axial slice and to take the sum as max(reg(x', y', z)). Here the asymmetry is approximated in the same axial slice mainly for the large slice thickness which makes grayscale interpolation in Z direction unreliable. As the asymmetry is used for detecting bright hemorrhage with respect to mirrored brain parenchyma, it is confined to be not less than 0.

Step #6: Calculate Grayscale Threshold haeTh, Threshold of Local Contrast lcTh, Threshold of Asymmetry asymTh, and Threshold of Partial Volume Voxels pvTh(z) for Bright Brain Regions Possible hemorrhage voxels in non-enhanced CT images appears bright. They are also brighter than their mirrored voxels with respect to the MSP (except special cases discussed in step #8). For a region of hemorrhage voxels, they are brighter than their neighboring non-hemorrhage voxels. These 3 features represent bright brain regions (BBRs) from different angles and are explored. In particular, the rough range of a parameter can be observed from literature, which in turn is used to approximate another parameter detailed below.

It is observed that the grayscale difference between a GM and a WM voxel is usually less than 20 from orgVolRaw(x, y,z). Thus voxels with the generalized asymmetry map asym (x, y, z) not less than 20 do not correspond to GM or WM voxels, instead, they are possible hemorrhage voxels. Thus a low bound can be set to confine the grayscale range of BBR voxels. A possible way can be: suppose that the grayscale mean and standard deviation of these voxels as $avg_1$ and $sd_1$, the grayscale threshold for BBR haeTh is calculated as $$haeTh=avg_1-sd_1 \qquad (3)$$

The threshold of local contrast IcTh and the threshold of asymmetry for BBRs are based on analysis of histograms, to be larger than those of typical brain voxels.

Figure 4:
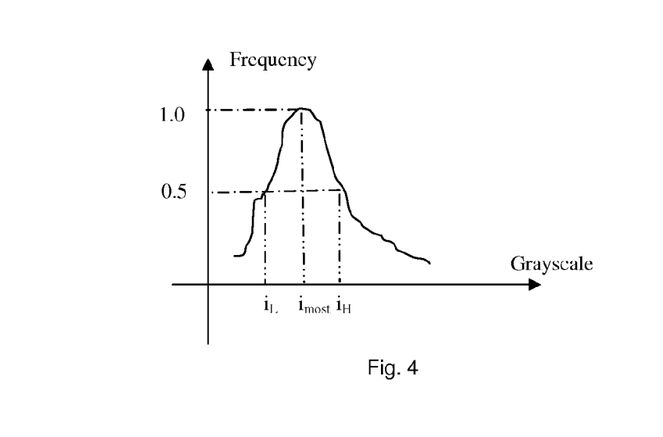
FIG. 4 shows a schematic histogram to determine the typical range $[i_L, i_H]$ of a distribution.

First, the typical brain voxels are identified below. Suppose the grayscale histogram of all the brain voxels is $hist_{brain}(i)$, the grayscale with the maximum frequency is $i_{most}$, the smallest grayscale with half of the maximum frequency is $i_L$, and the largest grayscale with half of the maximum frequency is $i_H$ (FIG. 4). Then $[0, i_L)$, $[i_L, i_H]$ and $(i_H, 255)$ can be taken as the low, typical and high grayscales of the brain, respectively.

For any brain voxel (x, y, z) with grayscale in the range of $[i_L, i_H]$, its local contrast is calculated as orgVolRaw(x, y, z) minus the minimum grayscale of its eight neighbors. The histogram of all the local contrast and the typical range of local contrast $[Ic_L, Ic_H]$ can be calculated. The threshold for local contrast IcTh should be larger than $Ic_H$, $$IcTh>Ic_H \qquad (4)$$

The threshold for asymmetry map asymTh can be determined in a similar way. For brain voxels with grayscale in the range of $[i_L, i_H]$, the typical asymmetry range $[asym_L, asym_H]$ can be found. asymTh should be larger than $asym_H$, $$asymTh>asym_H \qquad (5)$$

FIG. 4 shows a schematic histogram to determine the typical range $[i_L, i_H]$ of a distribution.

Through experiments, the two parameters (IcTh and asymTh) can be chosen as follow $$IcTh=Ic_H+5, asymTh=asym_H+5.$$

Step #7: Derive Initial Bright Brain Regions initBBR(x, y, z)

First a voxel-wise binarization is performed, imposing brightness and asymmetry constraints to get $B_4$(x, y, z). For any brain voxel (x, y, z), $B_4$(x, y, z) is set to 1 only when orgVolRaw(x,y,z) is not less than haeTh and asym(x,y,z) is not less than asymTh; otherwise $B_4$(x,y,z) is set to 0.

The foreground connected component of $B_4$(x, y, z) is found and its local contrast (the local contrast of a region is defined as the difference between the grayscale average of the region and the grayscale average of those voxels that do not belong to the region but are 8-connected neighbors of the region) is calculated. For any foreground connected component of $B_4$(x, y, z), if its local contrast is not less than IcTh, and the volume is not less than a constant (10 mm$^3$ for instance to exclude isolated noises), then this component is set as the foreground component of the initial bright brain regions initBBR(x, y, z). The other voxels are all set to 0.

Step #8: Recover Bright Brain Voxels Symmetrical to the MSP

Bright brain regions which have symmetrical voxels with respect to the MSP are 0 in initBBR(x, y, z) as they do not meet the asymmetry constraint. These regions correspond to cases when hemorrhage enters ventricles and most hemorrhage voxels should be in one hemisphere or the hemorrhage around the fourth ventricle and should be recovered as hemorrhage regions. They will be checked against the grayscale threshold (larger than haeTh), local contrast (larger than IcTh) and volumes (larger than 10 mm$^3$) stated below.

Figure 5A:
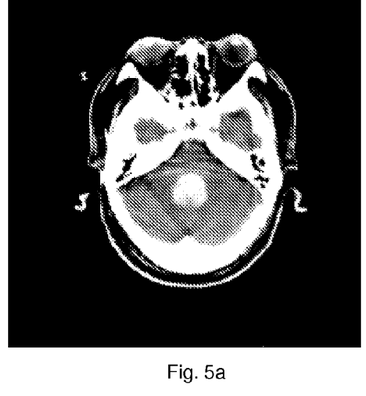
FIG. 5a shows an axial slice with hemorrhage into the fourth ventricle.
Figure 5B:
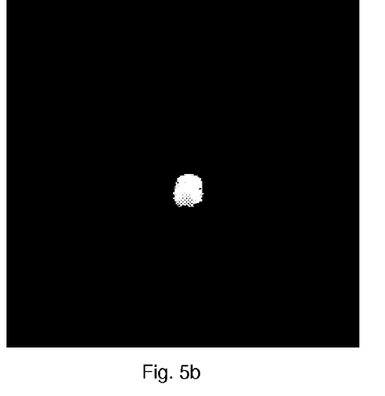

In the case of hemorrhage around the fourth ventricle, the BBR is roughly symmetrical around the MSP and the MSP passes through the BBR. Suppose the axial slice with the maximum brain area is $z_M$, then axial slice $z_p$ is found as the smallest z with the brain area being 0.8 times the area at slice $z_M$ ($z_p>z_M$). All the axial slices with $z>z_p$ are checked to find the bright regions which intersect with the MSP and meet the grayscale and local contrast constraints (i.e., the grayscales of all the voxels within the region are not less than haeTh, and the local contrast of the region is not smaller than IcTh). These bright regions are then added as the foreground regions of initBBR(x,y,z). FIGS. 5a and 5b show the recovery of a BBR around the fourth ventricle.

Figure 6A:
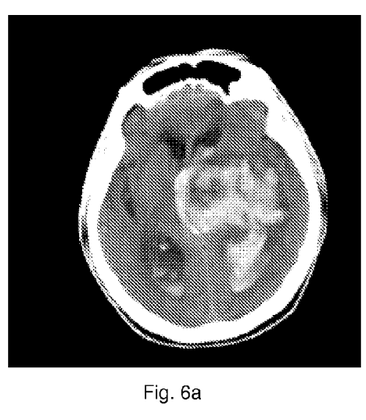
FIG. 6a shows an axial slice with some portion of the BBRs being symmetrical to the MSP which are recovered through imposing constraints on grayscale, local contrast and close to existing BBRs.
Figure 6B:
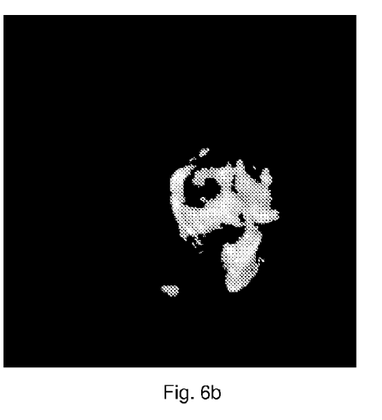

Other parts of the BBRs symmetrical to the MSP can be found in a different way. As the BBRs are mainly on one hemisphere, there must be asymmetrical BBR detected in initBBR(x, y, z). The missing BBRs can be detected this way: these regions meet the grayscale and local contrast constraints and close to some foreground voxels of initBBR(x, y, z) (two regions are close means that at least one voxel of a region could find an 8-neighbor from the other region). FIGS. 6a and 6b shows the recovery of this kind of BBR.

Step #9: Refinement

This is to refine the initial bright brain regions initBBR(x, y, z) to include those bright brain voxels on the border of BBRs and to exclude those bright voxels which may obviously correspond to non-hemorrhage voxels such as calcification.

Figure 7A:
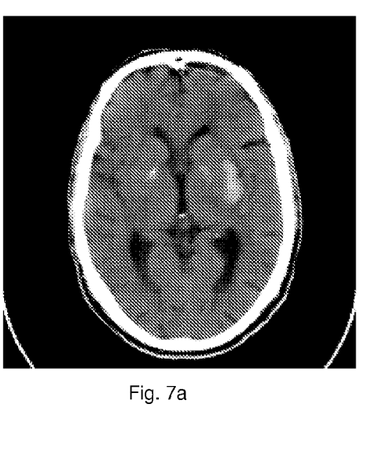
FIG. 7a shows symmetrical calcification around the basal gangalion and hemorrhage with asymmetrical bright brain region delineated.
Figure 7B:
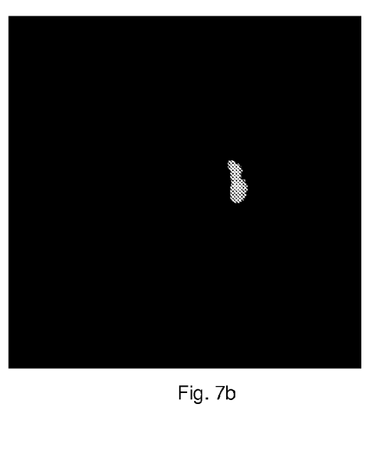

The first refinement is to exclude calcification which is high in grayscale, small in volume and symmetrical to the MSP. This can be achieved to check the volume (less than 150 mm$^3$ for example) and check the asymmetry in a larger window size (11×11 for example, also including upper and lower axial slices). If a foreground region in initBBR(x, y, z) has a volume less than 150 mm$^3$ and does not have a asymmetry map greater than asymTh, then this region is set as 0 of initBBR(x,y,z). FIG. 7 shows the symmetrical calcification can be effectively excluded.

FIGS. 7a and 7b show symmetrical calcification around the basal gangalion and hemorrhage with asymmetrical bright brain region delineated.

The second refinement is to recover those less bright brain voxels around the border of BBRs. This is achieved through checking the 5×5 neighborhood of initBBR(x,y,z)'s foreground border voxels. If a background voxel is within the 5×5 neighborhood and its grayscale is larger than (haeTh+fcmMean[3]+fcmSd[3])/2 (fcmMean[3] and fcmSd[3] are found in Step #4), this voxel contains at least half of the bright brain voxel and is taken as a bright brain voxel to be set as 1 in initBBR(x, y, z).

The last refinement is to compensate partial volume effect. Suppose along y direction initBBR(x, y, z) is 1, initBBR(x, y+1, z) is 0 and initBBR(x, y+2, z) is 0, then (x, y+1, z) will be changed to foreground voxel if $$orgVolRaw(x,y+1,z)>(haeTh+fcmMean[3]-fcmSd[3])/2, \text{ and}$$

$$orgVolRaw(x,y+1,z)>(orgVolRaw(x,y,z)+orgVolRaw(x,y+2,z))/2.$$

Similarly, other directions can be checked and compensated accordingly.

Lastly, check initBBR(x, y, z) to exclude all its foreground voxels with orgDV(x, y, z) greater than $T_{skull}$.

Step #10: Outputting

The constant ww (the constant of formula (2)) is changed adaptively according to the brightness of the detected bright brain regions (BBRs) and go back to the step#4: ww will be increased/decreased when the detected BBRs is low/high in average grayscale. For instance, if the average grayscale of the detected BBRs is smaller than a constant (160 from experiments), ww is decreased (changed to 75 for example), reflecting that the corresponding hemorrhage may be quite dark (i.e., hemorrhage is sub-acute phrase). On the contrary, if the average grayscale of the detected BBRs is high (such as above 200), ww is increased (to 90 for example), reflecting that the corresponding hemorrhage may be very bright and needs a larger window width.

Lastly, output the volume, localization and 3D shape of the BBRs.

The device for detecting the bright brain regions from computed tomography images comprises: an input unit loading computed tomography images data; a first deriving unit deriving the skull images; a second deriving unit deriving the brain images; a convertor converting said brain images to the lower bit images data; a first calculator calculating the generalized asymmetry map with respect to the midsagittal plane; a second calculator calculating grayscale threshold, threshold of local contrast, threshold of asymmetry, and threshold of partial volume voxels for bright brain regions; a third deriving unit derive initial bright brain regions; a recovering unit recovering bright brain voxels symmetrical to the midsagittal plane; a refining unit refining the initial bright brain regions; a judging unit checking if the detected BBRs is low or high in average grayscale and the window width being increased or decreased when the detected BBRs is low or high in average grayscale and going back to the converting step; and an output unit outputting the bright brain regions.

The first deriving unit derives the skull from said thresholding computed tomography images to contain all those voxels with a computed tomography value greater than a constant corresponding to the skull.

The second deriving unit comprises:
a threshold calculator applying Fuzzy c-means clustering to said thresholding computed tomography images to classify the volumetric data into clusters with ascending grayscales to get the low and high thresholds to remove non-brain tissues;
a binarization processor achieving the binarization through removing non-brain voxels to derive $B_1(x, y, z)$, i.e., $$B_1(x, y, z) = \begin{cases} 1, & \text{low threshold} < orgDV(x, y, z) < \text{high threshold} \\ 0, & \text{otherwise}; \end{cases}$$

a processing applying morphological opening with rectangular structuring element of side 4 mm to $B_1(x, y, z)$ to break the connection between the brain and non-brain tissues to get $B_2(x, y, z)$;

a finding apparatus finding the maximum foreground connected component of $B_2(x, y, z)$, whose holes are then filled to get $B_3(x, y, z)$;

a checking unit checking the neighboring axial slices of $B_3(x, y, z)$ to exclude isolated foreground regions of $B_3(x, y, z)$ to get the eventual brain mask Brain(x, y, z).

The low threshold is set as the maximum intensity of the first cluster and the high thresholds is set as the constant corresponding to the skull.

The isolated foreground region at the axial slice is a foreground region with less than half of the foreground voxels (x, y, z) having corresponding foreground voxels at its lower and upper axial slices.

The convertor converts said the 16-bit image data to 8-bit data.

The 8-bit brain data is formulated for both processing and monitoring with fixed window width through the following formula:

$$orgVolRaw(x, y, z) = \begin{cases} 0, & \text{Brain}(x, y, z) < 0 \\ 255 \times \frac{\text{Brain}(x, y, z)}{\text{window width}}, & 0 \leq \text{Brain}(x, y, z) \leq \text{window width} \\ 255, & \text{Brain}(x, y, z) > \text{window width} \end{cases}$$

where the window width is a constant and is changed adaptively according to the brightness of the detected bright brain regions The process of the first calculator comprises:
deriving the head mask through binarization of the computed tomography images;
Extracting the MSP by deriving from the computed tomography images through the following formula with the window width being constant corresponding to the skull:

$$orgVolRaw(x, y, z) = \begin{cases} 0, & \text{Brain}(x, y, z) < 0 \\ 255 \times \frac{\text{Brain}(x, y, z)}{\text{window width}}, & 0 \leq \text{Brain}(x, y, z) \leq \text{window width} \\ 255, & \text{Brain}(x, y, z) > \text{window width}; \end{cases}$$

defining the local symmetry as the sum of grayscale difference of plurality of pairs of searching line segments and outlier removal to handle abnormal grayscale distribution in axial slices;

if the number of inliers is less than 6, approximating each of the head mask as an ellipse with the long axis being taken as the approximated symmetry line segment to be used for approximating the MSP through outlier removal;

denoting the equation of the MSP as ax+by+cz+d=0, where a, b, c, d are calculated parameters with a>0, $a^2+b^2+c^2=1$, and x, y, z, and d all in mm;

the generalized asymmetry map being denoted as asym (x, y, z) and being calculated as $$asym(x, y, z) = \begin{cases} orgVolRaw(x, y, z) - \max(reg(x', y', z)), & orgVolRaw(x, y, z) > \max(reg(x', y', z)) \\ 0, & \text{otherwise} \end{cases}$$

where (x', y', z) is the mirrored point of (x, y, z) with respect to the intersection line at axial slice, max (reg (x', y', z)) is the maximum grayscale of orgVolRaw(x,y,z) within a neighborhood centered at (x',y',z).

Any voxel with a grayscale not less than $T_{low}$ is set to 1 and 0 otherwise; the maximum connected component of the binary image is found and holes within the maximum foreground component are filled to form the head mask.

Max(reg(x', y', z)) can be taken through calculating the grayscale average and standard deviation of this axial slice and to take the sum as max(reg(x', y', z)).

The process of the second calculator comprises:

supposing the grayscale mean and standard deviation of these voxels as $avg_1$ and $sd_1$, the grayscale threshold for BBR grayscale threshold being calculated as grayscale threshold=$avg_1$–$sd_1$;

the threshold of local contrast threshold of local contrast and the threshold of asymmetry for BBRs being based on analysis of histograms, to be larger than those of typical brain voxels, comprising:

the typical brain voxels being identified below, supposing the grayscale histogram of all the brain voxels is $hist_{brain}(i)$, the grayscale with the maximum frequency is $i_{most}$, the smallest grayscale with half of the maximum frequency is $i_L$, and the largest grayscale with half of the maximum frequency is $i_H$;

$[0, i_L]$, $[i_L, i_H]$ and $(i_H, 255)$ being taken as the low, typical and high grayscales of the brain, respectively;

for any brain voxel (x, y, z) with grayscale in the range of $[i_L, i_H]$, its local contrast being calculated as orgVolRaw (x, y, z) minus the minimum grayscale of its eight neighbors;

the histogram of all these local contrast and the typical range of local contrast $[Ic_L, Ic_H]$ being calculated, the threshold for local contrast threshold of local contrast being larger than $Ic_H$;

the threshold for asymmetry map threshold of asymmetry being determined as following: for brain voxels with grayscale in the range of $[i_L, i_H]$, the typical asymmetry range $[asym_L, asym_H]$ being found, threshold of asymmetry being larger than $asym_H$.

The process of the third deriving unit comprises:

a voxel-wise binarization being performed, imposing brightness and asymmetry constraints to get $B_4(x, y, z)$;

for any brain voxel (x, y, z), $B_4(x, y, z)$ being set to 1 only when orgVolRaw(x,y,z) is not less than haeTh and asym(x,y,z) is not less than asymTh, otherwise $B_4(x,y,z)$ being set to 0;

the foreground connected component of $B_4(x, y, z)$ being found;

the local contrast being defined as the difference between the grayscale average of the region and the grayscale average of those voxels that do not belong to the region but are 8-connected neighbors of the region;

for any foreground connected component of $B_4(x, y, z)$, if its local contrast is not less than threshold of local contrast, and the volume is not less than a constant, the component being set as the foreground component of the initial bright brain regions and the other voxels being all set to 0.

The process of the recovering unit comprises:

checking the bright brain regions against the grayscale threshold (larger than haeTh), local contrast (larger than IcTh) and volumes supposing the axial slice with the maximum brain area is $z_M$, the axial slice $z_p$ being found as the smallest z with the brain area being 0.8 times the area at slice $z_M$ if $z_p > z_M$;

checking all the axial slices with $z > z_p$ to find the bright regions which intersect with the MSP and meet the grayscale and local contrast constraints adding these bright regions as the foreground regions;

other parts of the BBRs symmetrical to the MSP being found in a different way;

detecting the missing BBRs which meet the grayscale and local contrast constraints and close to some foreground voxels.

The process of the refining unit comprises:

including the bright brain voxels on the border of BBRs and excluding the bright voxels which may obviously correspond to non-hemorrhage voxels such as calcification;

recovering the less bright brain voxels around the border of BBRs compensating partial volume effect;

excluding all its foreground voxels with computed tomography images greater than he constant corresponding to the skull.

The including step comprises: checking the volume and checking the asymmetry in a larger window size; If a foreground region in the initial bright brain regions has a volume smaller than a constant and does not have an asymmetry map greater than threshold of asymmetry, this region being set as 0 of the initial bright brain regions.

The recovering step comprises: checking the 5×5 neighborhood of the initial bright brain regions foreground border voxels; If a background voxel is within the 5×5 neighborhood and its grayscale is larger than (grayscale threshold+grayscale mean of the third cluster+standard deviation of the third cluster)/2, this voxel contains being at least half of the bright brain voxel and being taken as a bright brain voxel to be set as 1 in the initial bright brain regions.

Although only limited example embodiments are described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for detecting the bright brain regions from computed tomography images, comprising:
    loading computed tomography image data;
    deriving images of a skull;
    deriving brain images;
    converting the brain images to lower bit images data;
    calculating a generalized asymmetry map with respect to the midsagittal plane (MSP);
    calculating a grayscale threshold, a threshold of a local contrast, a threshold of asymmetry, and a threshold of partial volume voxels for bright brain regions (BBRs);
    deriving initial bright brain regions (BBRs);
    recovering bright brain voxels symmetrical to the midsagittal plane (MSP);
    refining the initial bright brain regions (BBRs);
    checking if detected bright brain regions (BBRs) is different from an average grayscale,
    increasing or decreasing a window width being increased or decreased when the detected bright brain regions (BBRs) is different from the average grayscale, then and going back to the converting step; and
    after checking to ensure that the bright brain regions (BBRs) match the average grayscale, outputting the bright brain regions (BBRs).

2. The method as claimed in claim 1, the step of deriving the skull images, further comprising:
    deriving the skull from the computed tomography images in which a threshold has been calculated, in order to contain each of the voxels with a computed tomography value greater than a constant corresponding to the skull.

3. The method as claimed in claim 1, wherein said step of deriving the brain images further comprises:

applying Fuzzy c-means clustering to the computed tomography images in which a threshold has been calculated, in order to classify the volumetric data into clusters with ascending grayscales to get low and high thresholds to remove non-brain tissues;

achieving the binarization through removing non-brain voxels to derive $B_1(x, y, z)$, i.e., $$B_1(x, y, z) = \begin{cases} 1, & \text{low threshold} < orgDV(x, y, z) < \text{high threshold} \\ 0, & \text{otherwise;} \end{cases}$$

applying a morphological opening with a rectangular structuring element with a side of 4 mm to $B_1(x, y, z)$ in order to break the connection between the brain and non-brain tissues to get $B_2(x, y, z)$;

finding a maximum foreground connected component of $B_2(x, y, z)$, holes of which are then filled to get $B_3(x, y, z)$; and checking neighboring axial slices of $B_3(x, y, z)$ to exclude isolated foreground regions of $B_3(x, y, z)$ to get the eventual brain mask (Brain) $(x, y, z)$.

4. The method as claimed in claim 3, wherein during said the step of deriving the brain images, the low threshold is set as a maximum intensity of a first one of the clusters, and the high threshold is set as a constant corresponding to the skull.

5. The method as claimed in claim 4, wherein during said step of deriving the brain images, each of the isolated foreground regions at the axial slice is a foreground region having fewer than half of the voxels (x, y, z) than in corresponding f ones of the voxels at its lower and upper axial slices.

6. The method as claimed in claim 1, wherein during said loading step, the brain images of 16-bit image data are converted to 8-bit data.

7. The method as claimed in claim 6, wherein during the converting step, the 8-bit brain data is formulated for both processing and monitoring with a fixed window width through the following formula:

$$orgVolRaw(x, y, z) = \begin{cases} 0, & \text{Brain}(x, y, z) < 0 \\ 255 \times \frac{\text{Brain}(x, y, z)}{\text{window width}}, & 0 \leq \text{Brain}(x, y, z) \leq \text{window width} \\ 255, & \text{Brain}(x, y, z) > \text{window width} \end{cases}$$

wherein the window width is a constant and is changed adaptively according to a brightness of the detected bright brain regions (BBRs).

8. The method as claimed in claim 1, the calculating step of the generalized asymmetry map further comprising:

deriving a head mask through binarization of the computed tomography images;

extracting the midsagittal plane (MSP) by deriving from the computed tomography images through a formula as follows, with the window width being a constant corresponding to the skull:

$$orgVolRaw(x, y, z) = \begin{cases} 0, & \text{Brain}(x, y, z) < 0 \\ 255 \times \frac{\text{Brain}(x, y, z)}{\text{window width}}, & 0 \leq \text{Brain}(x, y, z) \leq \text{window width} \\ 255, & \text{Brain}(x, y, z) > \text{window width}; \end{cases}$$

defining the local symmetry as a sum of a grayscale difference of a plurality of pairs of searching line segments, and removing in order to handle an abnormal grayscale distribution in axial slices; and wherein the generalized asymmetry map is denoted as asym $(x, y, z)$ and is calculated as:

$$asym(x, y, z) = \begin{cases} orgVolRaw(x, y, z) - \max(reg(x', y', z)), & orgVolRaw(x, y, z) > \max(reg(x', y', z)) \\ 0, & \text{otherwise} \end{cases}$$

wherein $(x', y', z)$ is the mirrored point of $(x, y, z)$ with respect to the intersection line at axial slice, max $(reg(x', y', z))$ is a maximum grayscale of orgVolRaw$(x,y,z)$ within a neighborhood centered at $(x',y',z)$.

9. The method as claimed in claim 8 wherein during the step of deriving the head mask, any of the voxels with a grayscale not less than $T_{low}$ is set to 1 and 0 otherwise; and a maximum connected component of the binary image is found and holes within a maximum foreground connected component are filled to form the head mask.

10. The method as claimed in claim 8, wherein between the defining step and the step of calculating the generalized asymmetry map, the calculating step further comprising:

approximating each of the head mask as an ellipse with the long axis being taken as an approximated symmetry line segment to be used for approximating the midsagittal plane (MSP) through outlier removal, if a number of inliers is less than 6; and denoting an equation of the midsagittal plane (MSP) as a $x+by+cz+d=0$, wherein a, b, c, d are calculated parameters with a>0, $a^2+b^2+c^2=1$, and x, y, z, and d are all in mm.

11. The method as claimed in claim 8 wherein during the calculating step of the generalized asymmetry map, max $(reg(x', y', z))$ can be obtained by calculating the grayscale average and a standard deviation of the axial slice and to obtain the sum as max $(reg(x', y', z))$.

12. The method as claimed in claim 8, the calculating step of calculating the thresholds, further comprising:

supposing the grayscale mean and a standard deviation of the voxels as $avg_1$ and $sd_1$, and calculating the grayscale threshold for the bright brain regions (BBRs) as a grayscale threshold=$avg_1-sd_1$;

basing the threshold of the local contrast and the threshold of asymmetry for the bright brain regions (BBRs on an analysis of histograms, to be larger than of typical brain voxels, and further comprising:
identifying the typical brain voxels by performing steps as follows:
supposing a grayscale histogram of each of the brain voxels is $hist_{brain}(i)$,
supposing a grayscale having the maximum frequency of $i_{most}$,
supposing a smallest grayscale having half of the maximum frequency of $i_L$, and
supposing a largest grayscale having half of the maximum frequency of $i_H$;
obtaining $[0, i_L)$, $[i_L, i_H]$ and $(i_H, 255)$ as low, typical and high grayscales of the brain, respectively;
calculating the local contrast for any brain voxel (x, y, z) with the grayscale in the range of $[i_L, i_H]$, by calculating the local contrast as orgVolRaw (x, y, z) minus a minimum grayscale as compared to eight neighbors;
calculating a histogram of each of the local contrasts and a typical range of the local contrasts $[lc_L, lc_H]$, the threshold of the local contrast being larger than contrast $lc_H$;
determining a threshold for an asymmetry map for brain voxels with the grayscale in the range of $[i_L, i_H]$, by finding a typical asymmetry range $[asym_L, asym_H]$,
the threshold of the asymmetry range being larger than $asym_H$.

13. The method as claimed in claim 8, the step of deriving initial bright brain regions (BBRs) further comprising:
performing a voxel-wise binarization,
imposing brightness and asymmetry constraints to get $B_4(x, y, z)$;
for any brain voxel setting (x, y, z), $B_4(x, y, z)$ set to 1 only when orgVolRaw (x,y,z) is not less than haeTh, and asym(x,y,z) is not less than asymTh, otherwise setting $B_4(x,y,z)$ to a setting of 0;
finding the foreground connected component of $B_4(x, y, z)$;
defining the local contrast as a difference between the grayscale average of the region and the grayscale average of the voxels that do not belong to the region but are 8-connected neighbors of the region; and
for any foreground connected component of $B_4(x, y, z)$, if the local contrast is not less than threshold of the local contrast, and the volume is not less than the constant,
setting the foreground connected component as the foreground connected component of the initial bright brain regions (BBRs), and
setting other voxels to the setting of 0.

14. The method as claimed in claim 8, the recovering step further comprising:
checking the bright brain regions (BBRs) against the grayscale threshold (larger than haeTh), the local contrast (larger than lcTh) and volumes;
supposing the axial slice with a maximum brain area is $z_M$, the axial slice $z_p$ being found as the smallest z with the brain area being 0.8 times the area at slice $z_M$ if $z_p > z_M$;
checking each of the axial slices with $z > z_p$ to find the bright brain regions (BBRs) which intersect with the midsagittal plane (MSP) and meet the grayscale and local contrast constraints;
adding the bright brain regions (BBRs) as the foreground regions;
finding other parts of the bright brain regions (BBRs) symmetrical to the midsagittal plane (MSP) in a different way; and
detecting the missing bright brain regions (BBRs) which meet the grayscale and local contrast constraints and close to some voxels in foreground regions.

15. The method as claimed in claim 1, the refining step further comprising:
including the bright brain voxels on a border of each of the bright brain regions (BBRs);
excluding the bright voxels which may obviously correspond to non-hemorrhage voxels such as calcification;
recovering fewer of the bright brain voxels around the border of bright brain regions (BBRs)
compensating for a partial volume effect; and
excluding the voxels in the foreground regions from the computed tomography images greater than the constant corresponding to the skull.

16. The method as claimed in claim 15, the including step further comprising:
checking the volume and checking the asymmetry in a larger window size; and
setting the initial bright brain regions (BBRs) to a setting of 0, if the volume of any of the foreground regions in the initial bright brain regions (BBRs) is smaller than the constant and does not have an asymmetry map greater than the threshold of asymmetry.

17. The method as claimed in claim 15, the recovering step further comprising:
checking a 5×5 neighborhood of foreground border voxels of the initial bright brain regions (BBRs), and
setting the initial bright brain regions (BBRs) to 1, if a background voxel is within a 5×5 neighborhood and the grayscale of the third cluster is larger than (grayscale threshold+grayscale mean of the third cluster+standard deviation of the third cluster)/2, and the voxel contains being at least half of the bright brain voxel, and
obtaining the background voxel as the bright brain voxel.

* * * * *